(12) United States Patent
Haase et al.

(10) Patent No.: US 8,545,484 B2
(45) Date of Patent: Oct. 1, 2013

(54) ACCUMULATOR FOR IMPLANTABLE INFUSION DEVICE

(75) Inventors: James M. Haase, Maplewood, MN (US); Ronald L. Mezera, Lake Elmo, MN (US); John M. Gray, Brooklyn Park, MN (US); Nicholas R. Whitehead, Hopkins, MN (US); Jeffrey P. Bodner, St. Paul, MN (US); Brian C. Egan, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 2 days.

(21) Appl. No.: 13/275,736

(22) Filed: Oct. 18, 2011

(65) Prior Publication Data

US 2013/0096503 A1    Apr. 18, 2013

(51) Int. Cl.
*A61K 9/22* (2006.01)

(52) U.S. Cl.
USPC ......... 604/891.1; 604/131; 604/151; 604/152

(58) Field of Classification Search
USPC  604/131, 135, 151, 152, 153, 288.01–288.04, 604/890.1, 891.1
See application file for complete search history.

(56) References Cited

U.S. PATENT DOCUMENTS

| | | | |
|---|---|---|---|
| 4,525,165 A | 6/1985 | Fischell | |
| 4,604,090 A * | 8/1986 | Reinicke | 604/118 |
| 4,655,765 A | 4/1987 | Swift | |
| 4,781,680 A | 11/1988 | Redmond et al. | |
| 5,281,210 A | 1/1994 | Burke et al. | |
| 5,797,733 A | 8/1998 | Falk et al. | |
| 6,293,922 B1 | 9/2001 | Haase | |
| 6,537,268 B1 | 3/2003 | Gibson et al. | |
| 6,572,583 B1 | 6/2003 | Olsen et al. | |
| 6,663,609 B2 | 12/2003 | Williamson et al. | |
| 2004/0260233 A1 | 12/2004 | Garibotto et al. | |
| 2007/0255234 A1 | 11/2007 | Haase et al. | |
| 2009/0227989 A1* | 9/2009 | Burke et al. | 604/891.1 |
| 2011/0166522 A1 | 7/2011 | Haase et al. | |

FOREIGN PATENT DOCUMENTS

DE    3518841 A1    11/1986
EP    1356837 A1    10/2003

* cited by examiner

*Primary Examiner* — Theodore Stigell
(74) *Attorney, Agent, or Firm* — Shumaker & Sieffert, P.A.

(57) ABSTRACT

An accumulator is employed in an implantable infusion device to provide compliance in the flow path of the device. The accumulator may act to increase the pumping accuracy and repeatability while simultaneously reducing the energy requirements of the device. In one example, the accumulator is arranged at the outlet of a fluid delivery pump of the infusion device. The accumulator includes a cover and a diaphragm biased away from the cover and configured to deflect toward the cover under pressure generated by the therapeutic agent in a flow path of the infusion device. The cover of the accumulator is configured to withstand the pressure generated by the therapeutic agent in the flow path without deforming.

31 Claims, 8 Drawing Sheets

ACCUMULATOR FOR IMPLANTABLE INFUSION DEVICE

TECHNICAL FIELD

This disclosure relates to implantable medical devices and, more particularly, to implantable infusion devices.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic agents, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic agent to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic agent, such as a drug, for delivery to a site in the patient. The fluid reservoir can be self-sealing and accessible through one or more ports. A pump is fluidly coupled to the reservoir for delivering the therapeutic agent to the patient. A catheter provides a pathway for delivering the therapeutic agent from the pump to the delivery site in the patient.

SUMMARY

The present disclosure is directed to accumulators employed in implantable infusion devices to provide compliance in the flow path of such devices, which may act to increase the pumping accuracy and repeatability of the devices while simultaneously reducing the energy requirements of the device. In one example, an accumulator in accordance with this disclosure is arranged at the outlet of a fluid delivery pump of the infusion device. The accumulator includes a cover and a diaphragm biased away from the cover and configured to deflect toward the cover under pressure generated by the therapeutic agent in a flow path of the infusion device. The cover of the accumulator is configured to withstand the pressure generated by the therapeutic agent in the flow path without appreciably deforming.

In one example, a fluid delivery pump for an implantable infusion device (IID) includes an inlet, an outlet, a pumping mechanism, and an accumulator. The inlet is configured to be fluidically connected to a source of a therapeutic agent. The outlet is configured to be fluidically connected to a catheter. The pumping mechanism is configured to receive the therapeutic agent from the source through the inlet and deliver the therapeutic agent through a flow path from the outlet into and through the catheter. The accumulator is arranged at the outlet of the fluid delivery pump. The accumulator includes a cover and a diaphragm biased away from the cover and configured to deflect toward the cover under pressure generated by the therapeutic agent in a flow path of the infusion device. The cover of the accumulator is configured to withstand the pressure generated by the therapeutic agent in the flow path without appreciably deforming.

In another example, an implantable infusion device includes a reservoir, a fluid delivery pump, and an accumulator. The reservoir is configured to store a therapeutic agent. The fluid delivery pump is configured to receive the therapeutic agent from the reservoir and deliver the therapeutic agent through an outlet of the fluid delivery pump into a flow path. The accumulator is arranged at the outlet of the fluid delivery pump. The accumulator includes a cover and a diaphragm biased away from the cover and configured to deflect toward the cover under pressure generated by the therapeutic agent in a flow path of the infusion device. The cover of the accumulator is configured to withstand the pressure generated by the therapeutic agent in the flow path without appreciably deforming.

In another example, a system includes an implantable infusion device (IID) and a catheter connected to the IID. The IID includes a reservoir, a fluid delivery pump, and an accumulator. The reservoir is configured to store a therapeutic agent. The fluid delivery pump is configured to receive the therapeutic agent from the reservoir and deliver the therapeutic agent through a flow path from an outlet of the fluid delivery pump into and through the catheter. The accumulator is arranged at the outlet of the fluid delivery pump. The accumulator includes a cover and a diaphragm biased away from the cover and configured to deflect toward the cover under pressure generated by the therapeutic agent in a flow path of the infusion device. The cover of the accumulator is configured to withstand the pressure generated by the therapeutic agent in the flow path without appreciably deforming.

The details of one or more examples are set forth in the accompanying drawings and the description below. Other features, objects, and advantages of examples according to this disclosure will be apparent from the description and drawings, and from the claims.

DETAILED DESCRIPTION

Figure 1:
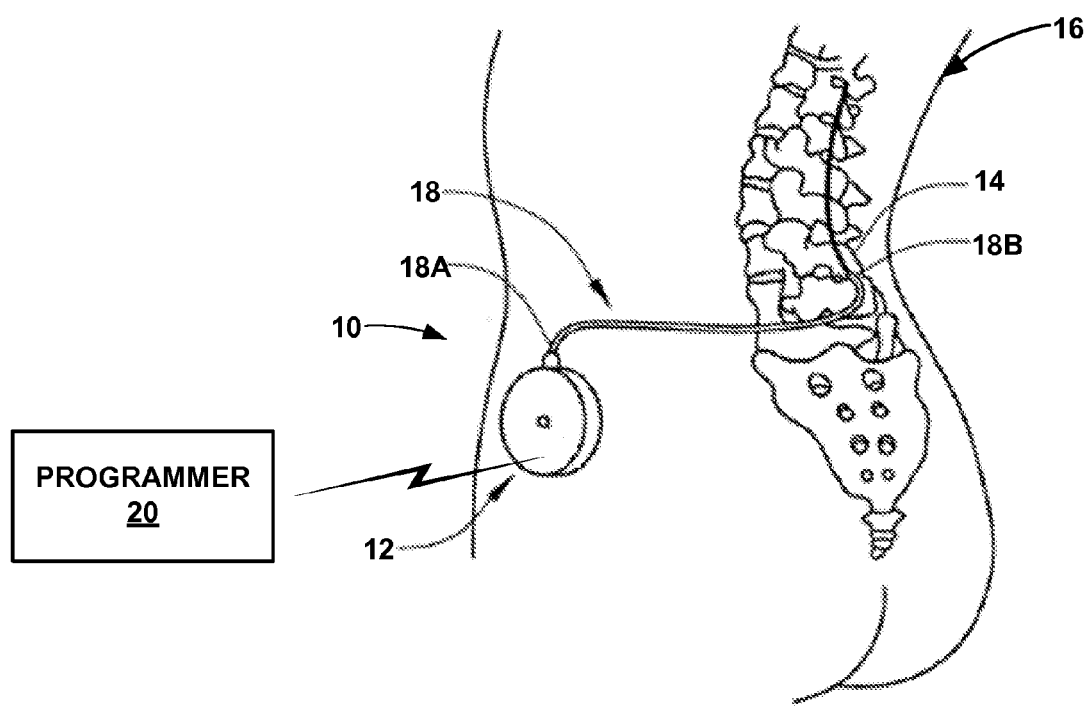
FIG. 1 is a conceptual diagram illustrating an example of a fluid delivery system including an implantable infusion device configured to deliver a therapeutic agent to a patient via a catheter.

The accuracy, repeatability, and efficiency of a fluid delivery pump of an implantable infusion device (IID), e.g. a drug infusion pump is a function of a number of factors. Operation of such fluid delivery pumps may, for example, be affected by a combination of flow resistance within a flow path of the IID through which the pump delivers a therapeutic agent, or other substance, e.g. saline, to a target location within a patient and a characteristic of the flow path known as "compliance." The flow path of an IID from the fluid delivery pump to the target delivery location may include one or more passages, channels, or conduits within the IID and a catheter connected to the IID and implanted, in whole or in part, within the patient.

Flow resistance is related to how much pressure is required to make a desired quantity of fluid flow through the path in a given time period. Compliance is related to how the component(s) that make up the flow path expands, contracts or deflects under pressure generated by a therapeutic agent, or other fluid flowing through the path. The compliance of the flow path may be a function of the cross-sectional area, e.g., the diameter of the catheter, as well as the properties of the material(s) from which different parts of the flow path are fabricated.

If a particular flow path (e.g. path from pump mechanism output port to distal end of a catheter) has little or no compliance, any attempt to move fluid into the flow path, e.g., at the pump mechanism outlet, will only occur to the extent that substantially an equivalent amount of fluid will be moved out of the flow path, e.g., out of the distal end of the catheter. On the other hand, if a flow path offers a large amount of compliance, a fluid may be easily pushed into one end of the flow path, with little or no fluid exiting the other end of the flow path during that time period.

In some pump designs too little compliance may influence the infusion pump's performance by offering increased resistance of flow at the inlet of the flow path (e.g. output port of the pump mechanism). If a significant amount of resistance is offered, the infusion pump mechanism may deliver less fluid, than predicted, for each pump stroke. It is further known that excessive compliance may influence the infusion pump mechanism's performance by offering insufficient resistance to flow at the inlet of the flow path (e.g. output port of the pump mechanism). A pump design with an improper amount of fluidic resistance, either too much or too little, may result in incorrect dosing of the fluid, which may have long term and short term health effects for a patient being treated by the fluid.

In accordance with the examples described in this disclosure, an IID includes a device arranged in the flow path of the IID that is configured as an accumulator for flow of a therapeutic agent through the fluid delivery device to a patient. Generally, an accumulator is an energy storage device. In hydraulic systems, an accumulator functions to store or absorb pressure of a non-compressible fluid. As used in this disclosure, accumulator is any device in a fluid flow system that creates compliance in the flow path of the system such that the accumulator is capable of absorbing pressure exerted on it by a fluid flowing along the path, or put another way, capable of absorbing part of the fluid volume of the fluid flowing through the flow path.

As noted above, configuring the flow path of an IID with the appropriate amount of compliance can increase the accuracy and repeatability by which the device delivers therapeutic agents to a patient. Additionally, the energy required to pump the therapeutic agent from the IID to the patient can be reduced by creating compliance in the flow path downstream of the pumping mechanism of the device. In this context, compliance means that some portion of the flow path is flexible or non-rigid. For example, the compliance may be sufficient to at least partially absorb the initial pressure spike/fluid volume generated by the delivery of a fluid pulse through the flow path by a pump within an IID, which, in turn, may reduce the energy required to drive the pump. Reducing the energy requirements of an IID may act to increase device longevity by reducing the load an internal power source that powers the pump, e.g., a battery of the device.

FIG. 1 is a conceptual diagram illustrating an example of a therapy system 10, which includes IID 12, catheter 18, and external programmer 20. IID 12 is connected to catheter 18 to deliver at least one therapeutic agent, e.g. a pharmaceutical agent, pain relieving agent, anti-inflammatory agent, gene therapy agent, or the like, to a target site within patient 16. IID 12 includes an outer housing that, in some examples, is constructed of a biocompatible material that resists corrosion and degradation from bodily fluids including, e.g., titanium or biologically inert polymers. IID 12 may be implanted within a subcutaneous pocket relatively close to the therapy delivery site. For example, in the example shown in FIG. 1, IID 12 is implanted within an abdomen of patient 16. In other examples, IID 12 may be implanted within other suitable sites within patient 16, which may depend, for example, on the target site within patient 16 for the delivery of the therapeutic agent. In still other examples, IID 12 may be external to patient 16 with a percutaneous catheter connected between IID 12 and the target delivery site within patient 16.

IID 12 delivers a therapeutic agent from a reservoir (not shown) to patient 16 through catheter 18 from proximal end 18A coupled to IID 12 to distal end 18B located proximate to the target site. Example therapeutic agents that may be delivered by IID 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy agents, anticoagulants, cardiovascular medications or chemotherapeutics.

Catheter 18 can comprise a unitary catheter or a plurality of catheter segments connected together to form an overall catheter length. External programmer 20 is configured to wirelessly communicate with IID 12 as needed, such as to provide or retrieve therapy information or control aspects of therapy delivery (e.g., modify the therapy parameters such as rate or timing of delivery, turn IID 12 on or off, and so forth) from IID 12 to patient 16.

Catheter 18 may be coupled to IID 12 either directly or with the aid of a catheter extension (not shown in FIG. 1). In the example shown in FIG. 1, catheter 18 traverses from the implant site of IID 12 to one or more targets proximate to spinal cord 14. Catheter 18 is positioned such that one or more fluid delivery outlets (not shown in FIG. 1) of catheter 18 are proximate to the targets within patient 16. In the example of FIG. 1, IID 12 delivers a therapeutic agent through catheter 18 to targets proximate to spinal cord 14.

IID 12 can be configured for intrathecal drug delivery into the intrathecal space, as well as epidural delivery into the epidural space, both of which surround spinal cord 14. In some examples, multiple catheters may be coupled to IID 12 to target the same or different nerve or other tissue sites within patient 16, or catheter 18 may include multiple lumens to deliver multiple therapeutic agents to the patient. Therefore, although the target site shown in FIG. 1 is proximate to spinal cord 14 of patient 16, other applications of therapy system 10 include alternative target delivery sites in addition to or in lieu of the spinal cord of the patient.

Programmer 20 is an external computing device that is configured to communicate with IID 12 by wireless telemetry. For example, programmer 20 may be a clinician programmer that the clinician uses to communicate with IID 12 and program therapy delivered by the IID. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IID 12. Programmer 20 may be a handheld or other dedicated computing device, or a larger workstation or a separate application within another multi-function device.

In examples according to this disclosure, IID 12 includes a fluid delivery pump withan inlet configured to be fluidically connected to a source of a therapeutic agent, e.g. a reservoir, an outlet configured to be fluidically connected to catheter 18, and a pumping mechanism configured to receive the therapeutic agent from the source through the inlet and deliver the therapeutic agent through a flow path from the outlet into and through the catheter. IID 12 also includes an accumulator that is arranged at the outlet of the fluid delivery pump. The accumulator of IID 12 includes a cover and a diaphragm. The diaphragm is biased away from the cover and configured to deflect under pressure generated by the therapeutic agent flowing through the flow path of the IID. The cover is configured to withstand the pressure generated by the therapeutic agent in the flow path without deforming, or, at the least, without appreciably deforming. In other words, while the cover may not be completely indifferent to the pressure in the flow path generated by the therapeutic fluid, the cover will nevertheless remain substantially rigid, especially relative to the flexibility of the diaphragm. In one example, deflection of the cover may not be perceivable by the human eye and the cover may thus appear to an observer to not deflect under the pressure generated by the therapeutic fluid flowing through the flow path. As explained in greater detail with reference to FIGS. 3-7D below, accumulators according to this disclosure are arranged within the IID and configured to improve the accuracy, repeatability, and efficiency of the pump of the IID.

Figure 2:
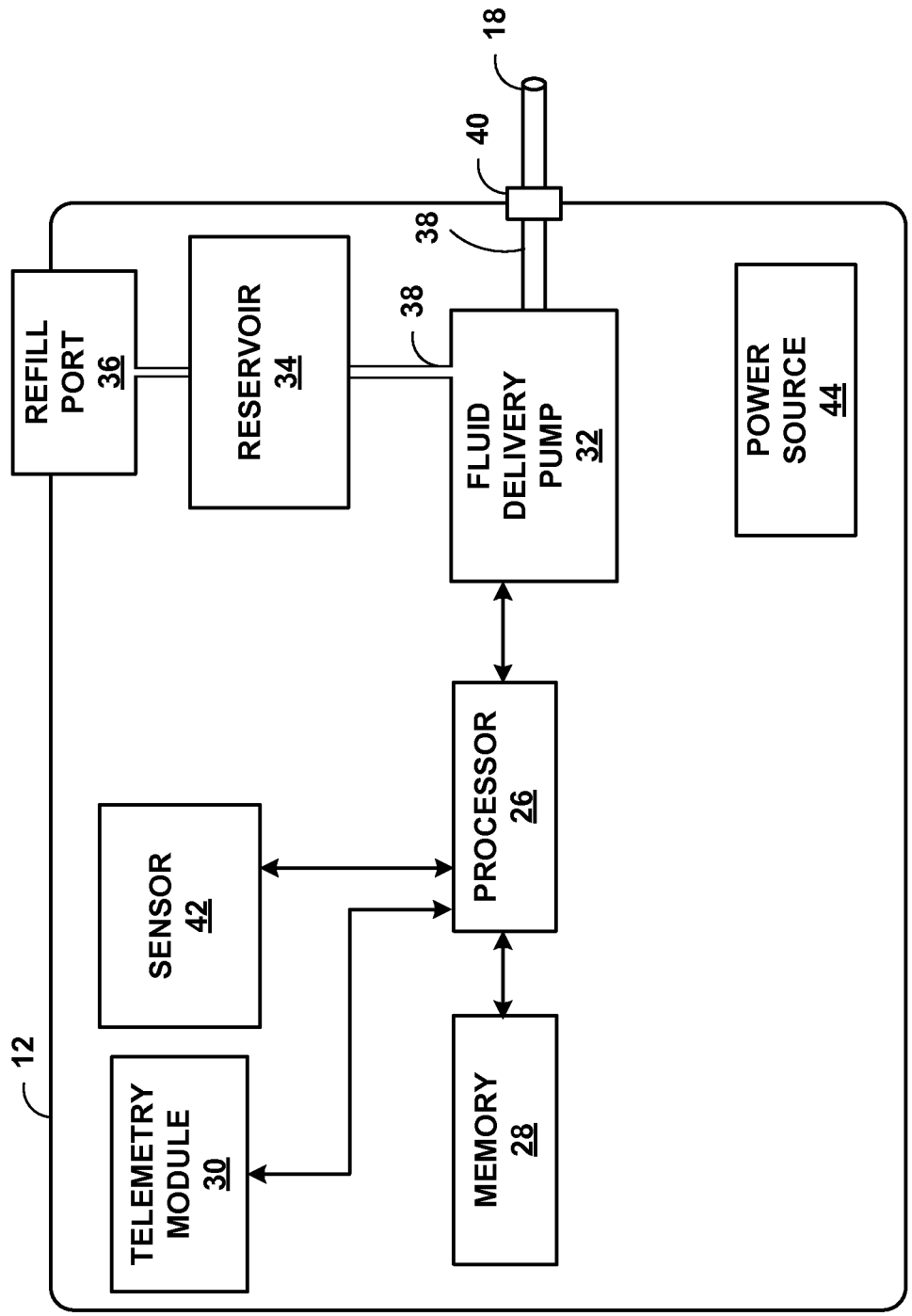
FIG. 2 is functional block diagram illustrating an example of the implantable infusion device of FIG. 1.

FIG. 2 is a functional block diagram illustrating components of an example of IID 12, which includes processor 26, memory 28, telemetry module 30, fluid delivery pump 32, reservoir 34, refill port 36, internal passage 38, catheter access port 40, sensor 42, and power source 44. Processor 26 is communicatively connected to memory 28, telemetry module 30, and fluid delivery pump 32. Fluid delivery pump 32 is connected to reservoir 34 and internal passage 38. Reservoir 34 is connected to refill port 36. Catheter access port 40 is connected to internal passage 38 and catheter 18. IID 12 also includes power source 44, which is configured to deliver operating power to various components of the IID.

In some examples, IID 12 may include a plurality of reservoirs for storing more than one type of therapeutic agent. However, for ease of description, an IID 12 including a single reservoir 34 is primarily described with reference to the disclosed examples.

During operation of IID 12, processor 26 controls fluid delivery pump 32 with the aid of instructions associated with program information that is stored in memory 28 to deliver a therapeutic agent from reservoir 34 to patient 16 via catheter 18. Instructions executed by processor 26 may, for example, define therapy programs that specify the dose of therapeutic agent that is delivered to a target tissue site within patient 16 from reservoir 30 via catheter 18. The programs may further specify a schedule of different therapeutic agent rates and/or other parameters by which IID 12 delivers therapy to patient 16. Therapy programs may be a part of a program group, where the group includes a number of therapy programs. Memory 28 of IID 12 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IID 12, e.g., via external programmer 20 at any time during therapy or as designated by the clinician.

Components described as processors within IID 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 28 of IID 12 may store instructions for execution by processor 26 including, e.g., therapy programs and/or program groups and any other information regarding therapy delivered to patient 16 and/or the operation of IID 12. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy.

Awareness of different properties within or related to the operation of IID 12 including, e.g., fluid flow rates, pressures, temperatures, volumes, and the like, may be desirable to monitor during operation of the device. Consequently, IID 12, in various examples, may include one or more sensor(s) 42, which may be arranged in a number of locations within IID 12, including, e.g., in reservoir 34, or a fluid pathway of the device, e.g. within a lumen of catheter 18 or refill port 36. In some examples, the sensor is configured to measure a fluid characteristic in IID 12. In some examples, the sensor may include a pressure sensor, flow sensor, pH sensor, temperature sensor or the like. In any event, IID 12 may include multiple sensors, e.g., to measure different fluid characteristics or to measure fluid characteristics in multiple locations, or to measure physiological parameters of the patient within which the device is implanted.

At various times during the operation of IID 12 to treat patient 16, communication to and from IID 12 may be necessary to, e.g., change therapy programs, adjust parameters within one or more programs, configure or adjust a particular bolus, or to otherwise download information to or from IID 12. Processor 26 controls telemetry module 30 to wirelessly communicate between IID 12 and other devices including, e.g., programmer 20. Telemetry module 30 in IID 12, as well as telemetry modules in other devices described in this disclosure, such as programmer 20, can be configured to use RF communication techniques to wirelessly send and receive information to and from other devices respectively. In addition, telemetry module 30 may communicate with programmer 20 via proximal inductive interaction between IID 12 and the external programmer. Telemetry module 30 may send information to external programmer 20 on a continuous basis, at periodic intervals, or upon request from the programmer.

Power source 44 delivers operating power to various components of IID 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IID 12. In some examples, power requirements may be small enough to allow IID 12 to utilize patient motion and implement a kinetic energy-scavenging device to trickle charge a rechargeable battery. In other examples, traditional batteries may be used for a limited period of time. As another alternative, an external inductive power supply could transcutaneously power IID 12 as needed or desired.

Figure 3A:
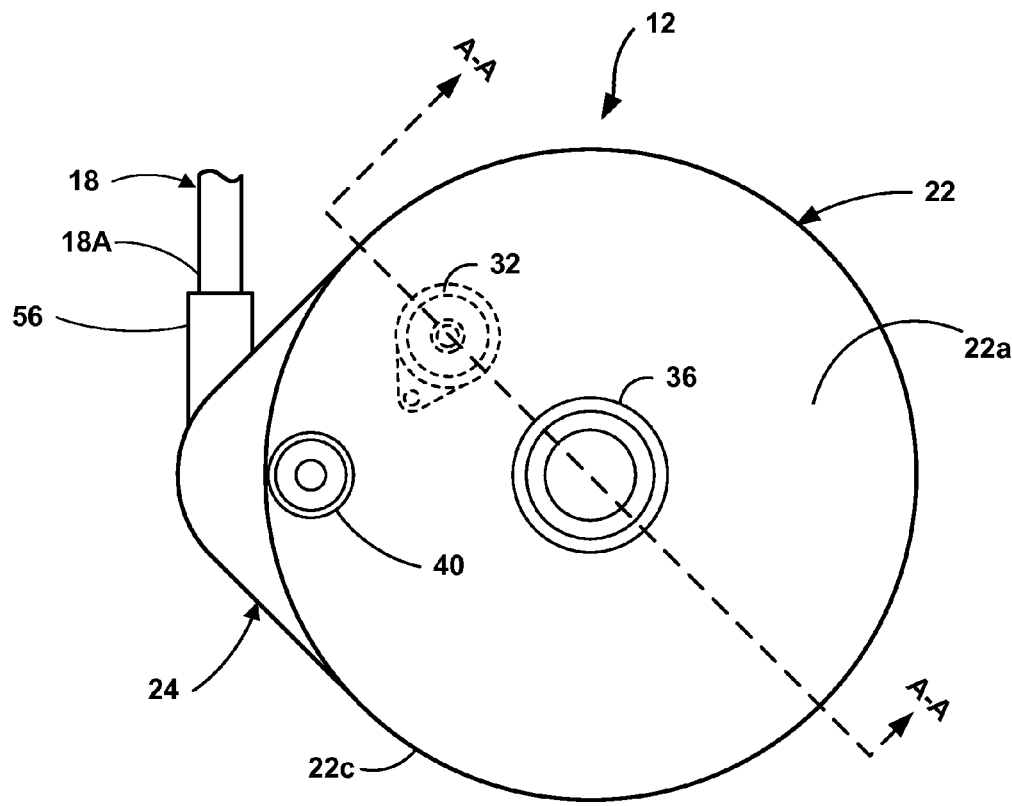
FIG. 3A is a plan view illustrating an example configuration of the implantable infusion device of FIG. 1.
Figure 3B:
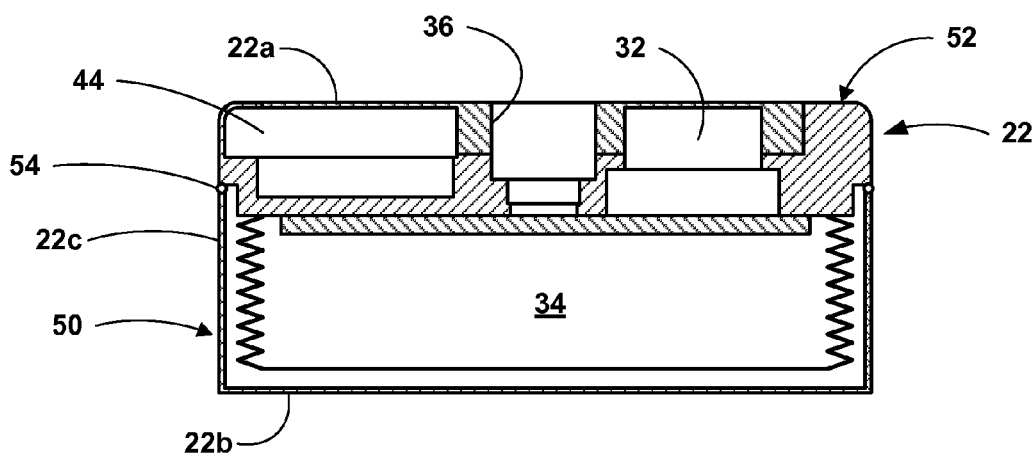
FIG. 3B is a cross-sectional side view of the example implantable infusion device of FIG. 2A cut along the section line A-A of FIG. 3A.

FIGS. 3A and 3B illustrate an example configuration of IID 12 including housing 22, header 24, pump 32, and reservoir 34, refill port 36, catheter access port (CAP) 40, and power source 44. FIG. 3A is a plan view of IID 12 and FIG. 3B is a section view of IID 12 cut along section line A-A in FIG. 3A. In FIGS. 3A and 3B, housing 22 of IID 12 is generally cylindrical, including two circular ends 22a, 22b (only one of which is visible in the view of FIG. 3A) connected to one another by annular wall 22c. Housing 22 is divided into two parts, which include shield 50 and bulkhead 52. Shield 50 and bulkhead 52 of housing 22 are connected at seam 54. In one example, seam 54 includes a weld joint that is configured to create a hermetic seal between shield 50 and bulkhead 52. Housing may be constructed from biocompatible materials that resist corrosion and degradation from bodily fluids including, e.g., titanium or biologically inert polymers. Housing may be fabricated using a variety of solid material manufacturing techniques, including, e.g. pressing, casting, molding, or any one or more of various material removal processes, including, e.g., milling, turning, grinding, electrical discharge machining (EDM), or laser or torch cutting. For example, shield 50 may be pressed from sheet stock of a metal or metal alloy, e.g. a titanium alloy, while bulkhead 52 is machined from stock piece of a similar or different material. In another example in which part or all of housing 22 is fabricated from a plastic, shield 50 and/or bulkhead 52 may be manufactured using injection molding techniques.

In one example, shield 50 is a thin wall enclosure that receives and surrounds reservoir 34 of IID 12 (see FIG. 3B). The space between the inner surfaces of the walls of shield 50 and the reservoir of IID 12 defines a chamber within which a propellant gas is held at pressure. The propellant gas in the gas chamber within shield 50 is employed to regulate the pressure within the reservoir of IID 12. Bulkhead 52 houses a number of components of IID 12 including, e.g., control electronics, e.g. processor(s), memory, and telemetry, as well as fluid delivery pump 32, power source 44, and one or more sensors.

Header 24 includes a catheter junction (not shown) and is connected to housing 22 of IID 12 generally along a portion of annular side wall 22c. Header 24 forms the connection between IID 12 and a catheter through which the device delivers a therapeutic agent to a patient, e.g. catheter 18 of FIG. 1. Tubes and/or passages in header 24 and bulkhead 52 provide a fluid connection between the outlet of fluid delivery pump 32 of IID 12 and catheter 18, which is either directly connected or indirectly connected via extension 56.

As noted above, housing 22 of IID 12 is generally cylindrical, including two circular ends 22a, 22b connected to one another by annular side 22c. In FIG. 3B, shield 50 includes one of the two generally circular ends 22b of housing 22, and bulkhead 52 includes the other circular end 22a of housing 22. Shield 50 also includes a portion of annular side 22c below seam 54 in the view of FIG. 3B, while the remaining portion of annular side 22c of housing 22 is part of bulkhead 52, i.e. above seam 54 in the view of FIG. 3B.

Refill port 36 of IID 12 is arranged in bulkhead 52 near the center of circular wall 22a. Refill port 36 is connected to reservoir 34. Periodically, fluid may need to be supplied percutaneously to the reservoir of IID 12 because all of a therapeutic agent has been or will be delivered to patient 16, or because a clinician wishes to replace an existing fluid with a different fluid or similar fluid with different concentrations of therapeutic ingredients. Refill port 36 can therefore comprise a self-sealing membrane, or septum to prevent loss of therapeutic agent delivered to the reservoir via refill port 36. For example, after a percutaneous delivery system, e.g., a hypodermic needle, penetrates the membrane of refill port 36, the membrane may seal shut when the needle is removed from refill port 36.

Catheter access port 40 is arranged in bulkhead 52 of IID 12 near the perimeter of circular wall 22a. Catheter access port 40 is connected to internal passage 38, which may include, e.g., internal tubing and/or channels in bulkhead 52 and from there to a delivery catheter that is connected to IID 12 via catheter junction 56 of header 24. Clinicians or other users may access a catheter connected to IID 12 directly via catheter access port 40, e.g., to flush the catheter with saline, deliver a therapeutic agent directly to the patient via the catheter, or in the process of executing bridging bolus.

During operation of IID 12, the device, e.g. processor 26 controls fluid delivery pump 32 with the aid of instructions associated with program information, e.g. information stored memory 28 of the device, to deliver a therapeutic agent to patient 16 via catheter 18. Instructions executed by processor 26 of IID 12 may, for example, define therapy programs that specify the dose of therapeutic agent that is delivered to a target tissue site within patient 16 from reservoir 30 via catheter 18. The programs may further specify a schedule of different therapeutic agent rates and/or other parameters by which IID 12 delivers therapy to patient 16.

Fluid delivery pump 32 draws fluid from reservoir 34 through an inlet of the pump and pumps the fluid out of an outlet of the pump through internal passage 38, which may include, e.g., internal tubing and/or channels in bulkhead 52 of housing 22 of IID 12 to catheter 18 through which the fluid is delivered to patient 16 to effect one or more of the treatments described above, e.g. in accordance with a program stored on memory of the IID. Fluid delivery pump 32 can be any mechanism that delivers a therapeutic agent in some metered or other desired flow dosage to the therapy site within patient 16 from reservoir 30 via implanted catheter 18. In one example, fluid delivery pump 32 is a squeeze pump that squeezes internal tubing, which may form part of internal passage 38 in a controlled manner, e.g., such as a peristaltic pump, to progressively move fluid from reservoir 34 to the distal end of catheter 18 and then into patient 16 according to parameters specified by the therapy program stored on memory 28 and executed by processor 26. In various examples, fluid delivery pump 32 may be an axial pump, a centrifugal pump, a pusher plate pump, a piston-driven pump, or other means for moving fluid through internal passage 38 and catheter 18. In one example, fluid delivery pump 32 is an electromechanical pump that delivers fluid by the application of pressure generated by a piston that moves in the presence of a varying magnetic field and that is configured to draw fluid from reservoir 34 and pump the fluid through internal tubing or cavities in bulkhead 52 and catheter 18 to patient 16.

In examples according to this disclosure, IID 12 includes an accumulator that is arranged at the outlet of fluid delivery pump 32 along the internal passage 38 defining the fluid flow path between pump 32 and proximate end 18A of catheter 18. The accumulator of IID 12 includes a cover and a diaphragm. The diaphragm is biased away from the cover and configured to deflect under pressure generated by the therapeutic agent in the flow path of the IID. The cover is connected to bulkhead 52, e.g., welded to the bulkhead. The cover is configured to withstand the pressure generated by the therapeutic agent in the flow path without deforming. For example, the cover is sized, shaped, and constructed from a material that allows the cover to withstand the pressure generated by the therapeutic agent in the flow path without deforming. As fluid delivery pump 32 draws fluid from reservoir 34 through an inlet of the pump and pumps the fluid out of an outlet of the pump through internal tubing or cavities in bulkhead 52 to catheter 18, the diaphragm of the accumulator deflects under the pressure the therapeutic agent flowing through IID 12. In this manner, the accumulator may function to provide compliance in the flow path of IID 12 to improve the accuracy of the metered delivery of therapeutic agent to patient 16 by pump 32 and reduce the energy required to drive the pump.

As illustrated in FIG. 3B, reservoir 34 includes an expandable and contractible bellows, the pressure of which is maintained via a propellant, e.g. a propellant gas. The propellant gas acts as a pressure-providing means to the chamber of reservoir 34, which regulates the pressure within the reservoir by applying pressure to the flexible bellows structure to discharge the therapeutic agent stored in the reservoir through internal passage 38 to fluid delivery pump 32. In one example, the propellant gas is employed to maintain a substantially constant pressure within reservoir 34 in order to deliver the therapeutic agent through tubing or cavities in bulkhead 52 to pump 32 consistently and accurately over time. The propellant gas is held within the chamber surrounding reservoir 34, which is defined by the inner walls of shield 50 of housing 22 of IID 12. The propellant gas used to regulate the pressure of reservoir 34 of IID 12 may be a fluid that is in phase change between a liquid state and a gas state when, e.g., in equilibrium between phases at around 35-37 degrees Celsius which is a common temperature range of the body of patient 16. The propellant gas employed in examples of IID 12 may comprise at least one of butane, perflurohexane, or perfluropentane.

Figure 4:
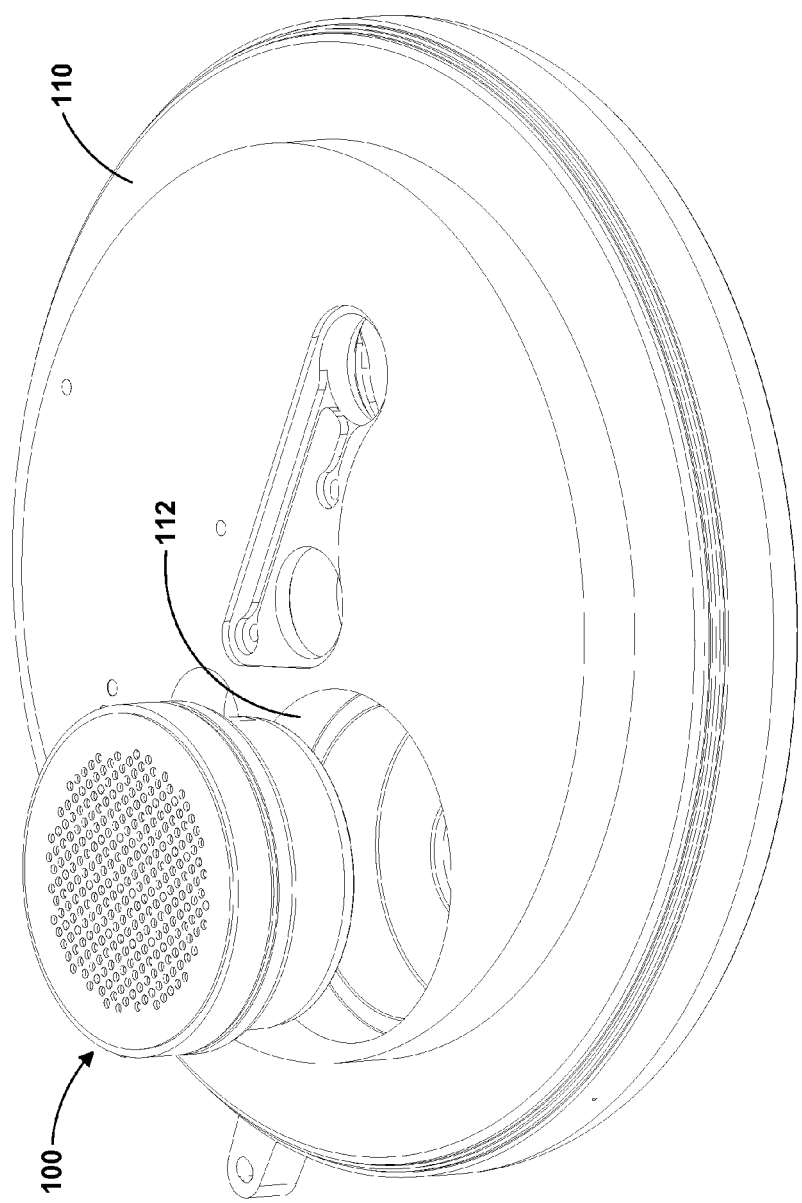
FIG. 4 is a partially exploded view illustrating an example fluid delivery pump and bulkhead of an implantable infusion device.
Figure 5:
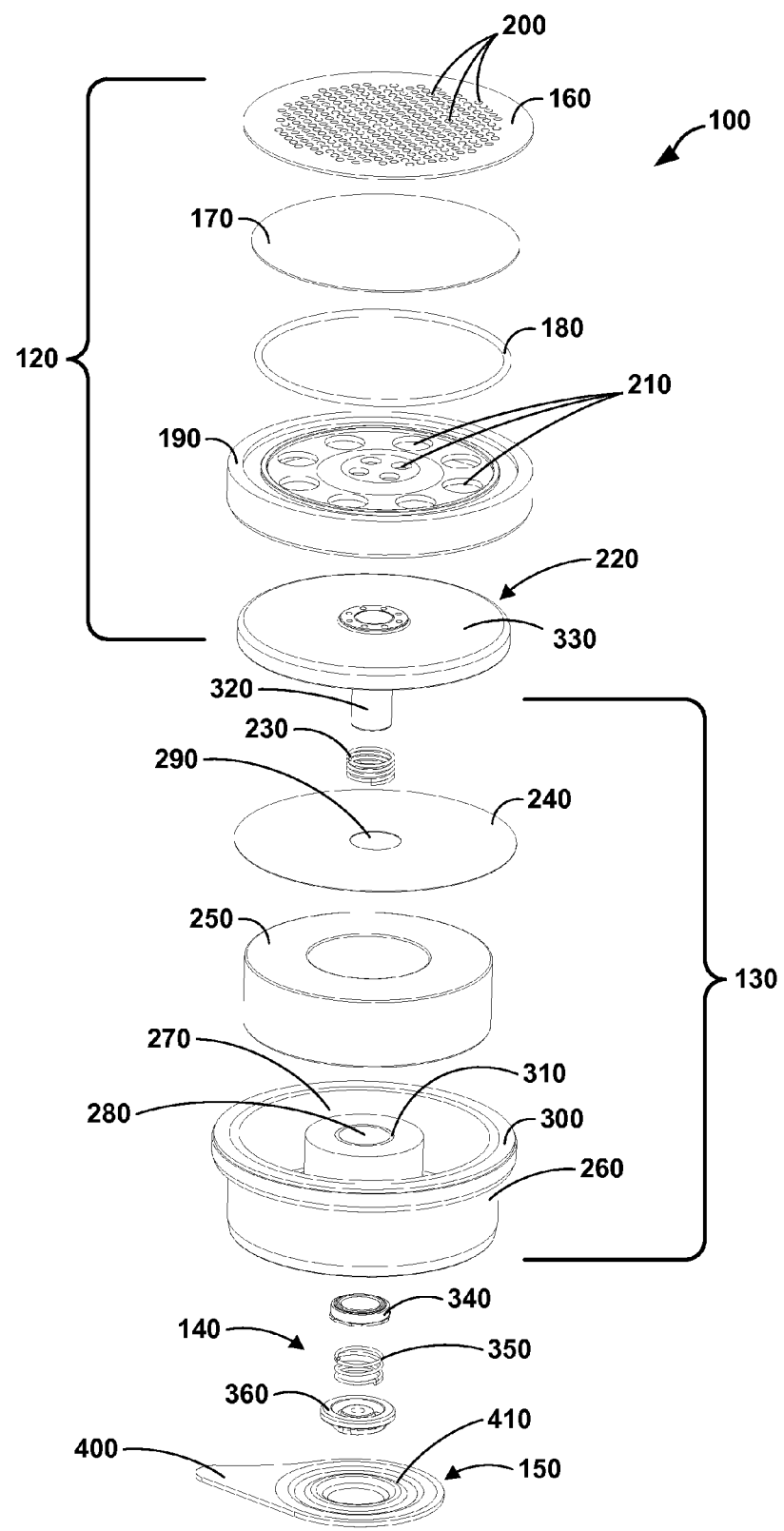
FIG. 5 is an exploded view of the fluid delivery pump of FIG. 4.
Figure 6:
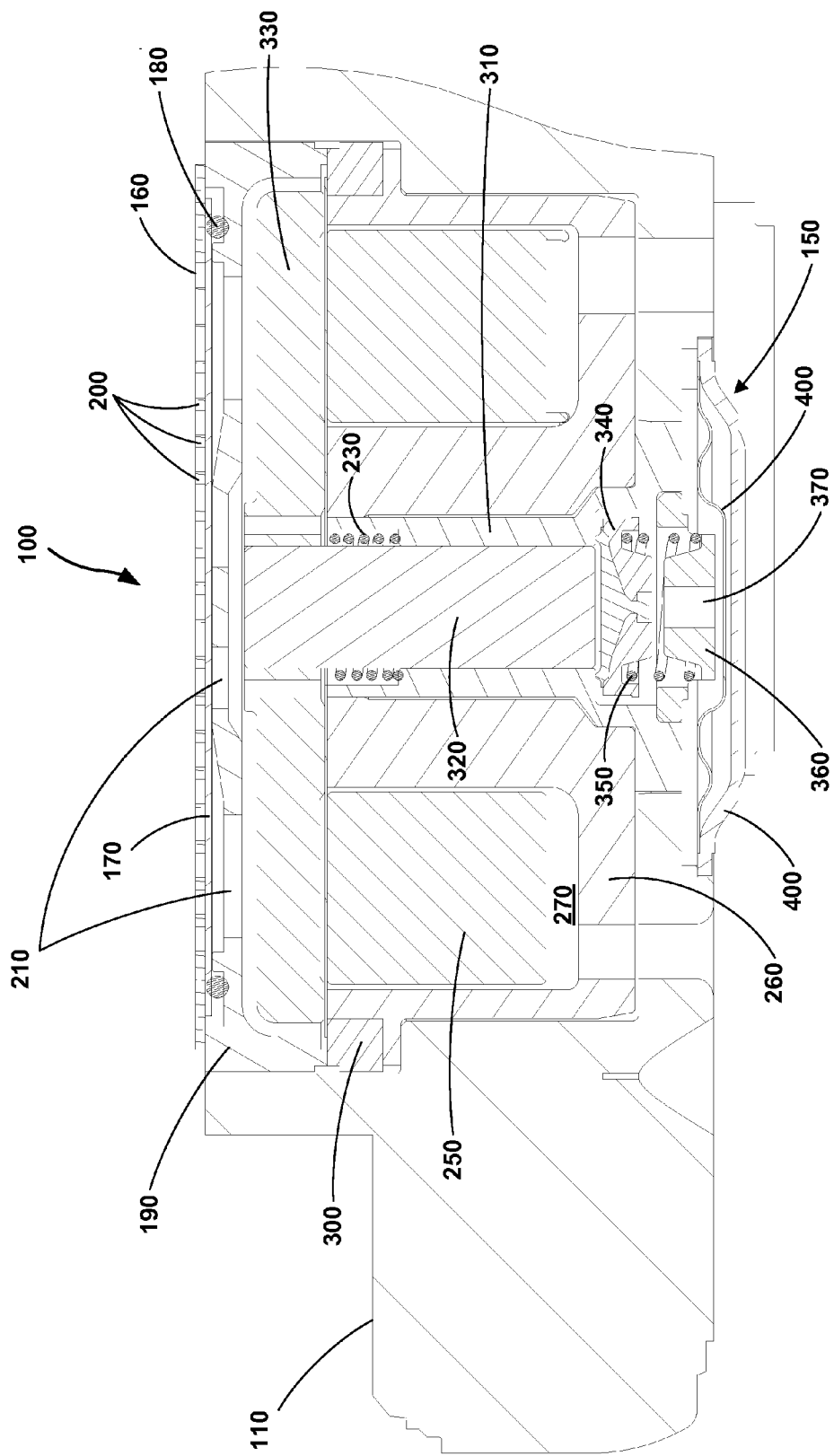
FIG. 6 is a section view of the pump mounted in the bulkhead of FIG. 4.

FIGS. 4-6 illustrate components of an example of fluid delivery pump 100, which is configured to be mounted in bulkhead 110. FIG. 4 is a partially exploded view illustrating fluid delivery pump 100 and bulkhead 110. FIG. 5 is an exploded view of fluid delivery pump 100. FIG. 6 is a section view of pump 100 mounted in bulkhead 110. Pump 100 and bulkhead 110 may be part of an IID, such as IID 12 (FIGS. 1-3B).

As shown in FIG. 4, bulkhead 110 includes mounting bay 112 to receive fluid delivery pump 100. As described above, a reservoir may be connected to bulkhead 110 and surround pump 100. During operation of the IID, pump 100 may draw a therapeutic agent from the reservoir and pump the agent out of a catheter to a target delivery site within a patient. Consistent with bulkhead 52 described above with reference to FIGS. 3A and 3B, bulkhead 110 of FIGS. 4 and 6 includes a biocompatible material, e.g. a stainless steel alloy, a titanium alloy or other biocompatible material.

In FIG. 5, pump 100 is illustrated in an exploded view to reveal the components that comprise the pump including cover 120, pumping mechanism 130, check valve 140. An example accumulator 150 in accordance with this disclosure is also illustrated with pump 100 in FIG. 5. Cover 120 of pump 100 defines the fluid inlet of the pump and check valve 140 defines the fluid outlet of the pump. During the operation of fluid delivery pump 100, therapeutic agent flows through holes 200, filter 170 and holes 210 in base 190 of cover 120 into an enclosure of pumping mechanism. Once within the enclosure under cover 120, the agent is pushed by pumping mechanism 120 through check valve 140. After passing through valve 140, the therapeutic agent is directed to one or more target sites within a patient, e.g. via internal tubing or cavities (e.g. which may be included in internal passage 38 described with reference to FIG. 2) within bulkhead 110 and a catheter.

Cover 120 includes perforated screen 160, filter element 170, gasket 180 and base 190. Gasket 180 forms a seal between filter element 170 and base 190 to prevent any therapeutic agent flowing through pump 100 from bypassing filter element 170. Perforated screen 160 serves to compress filter element 170 and gasket 180 to provide a seal between filter element 170 and gasket 180 as well as a seal between gasket 180 and base 190. As the components of cover 120 are within the flow path of fluid being pumped by fluid delivery pump 100, the components of the cover include biocompatible materials. As examples, perforated screen 160 and base 190 may comprise a stainless steel, titanium alloy or other suitable material. As another example, perforated screen 160 and base 190 may comprise a polymer, a stainless steel or other suitable material. In addition, gasket 180 may comprise a deformable biocompatible material, such as a polymer, silicon rubber or other suitable material. Holes 200 in perforated screen 160 and holes 210 in base 190 provide the fluid flow path through cover 120, which defines the inlet of pump 100 through which therapeutic agent is delivered by the pump from the reservoir of the IID in which pump 100 is arranged, e.g., reservoir 34 of IID 12 in FIGS. 3A and 3B.

Pumping mechanism 130 of fluid delivery pump 100 includes an electromagnetic piston pump that is configured to deliver therapeutic agents from a reservoir through a catheter of an IID by applying a current to an electromagnetic coil that causes a piston to pump the agent through the flow path of the IID. In FIG. 5, pumping mechanism 130 includes piston/pole assembly 220, piston spring 230, barrier plate 240, electromagnetic coil 250, and magnetic cup 260. Barrier plate 240 is employed in fluid delivery pump 100 to act as a fluidic barrier between a flow path through the pump and electromagnetic coil 250 and magnetic cup 260. For example, barrier plate 240 may be welded to base 190 of cover 120 and a weld ring fit to magnetic cup 260 to form a hermetic seal between the flow path of the therapeutic agent and electromagnetic coil 250.

Magnetic cup 260 forms recess 270 and central aperture 280. Recess 270 of magnetic cup 260 is sized and shaped to receive electromagnetic coil 250. Central aperture 280 defines part of the flow path through which piston/pole assembly pumps therapeutic agent through check valve 140. Magnetic cup 260 may be fabricated from a highly magnetic material. The highly magnetic material of magnetic cup 260 efficiently magnetizes in response to current through electromagnetic coil 250. As an example, magnetic cup 260 may include a highly magnetic steel alloy. As another example, magnetic cup 260 may include a highly magnetic stainless steel alloy such as 430F. However, as highly magnetic materials are generally susceptible to corrosion, magnetic cup 260 may be separated from the flow path of fluid being pumped by fluid delivery pump 100 to prevent corrosion of magnetic cup 260. For example, magnetic cup and electromagnetic coil 250 may be separated from the flow path of pump 100 at least in part by barrier plate 240.

Electromagnetic coil 250 includes one or more insulated conductors arranged in a multitude of turns. As examples, electromagnetic coil 250 may include a single continuous conductor or more than one conductor electrically connected in series or in parallel. Electromagnetic coil 250 may be connected to a flex circuit that provides the electrical connections used to deliver current to electromagnetic coil 250. Within fluid delivery pump 100, delivering current to electromagnetic coil 250 magnetizes magnetic cup 260 in order to attract pole 330 for a pump stroke of fluid delivery pump 100.

Barrier plate 240 covers recess 270 to enclose electromagnetic coil 250 within recess 270. Barrier plate 240 forms mating aperture 290, which is arranged to coincide with central aperture 280 of magnetic cup 260. In some examples, magnetic cup 260 may include weld ring 300 and sleeve 310, which are joined to magnetic cup and provide a material structure to which barrier plate 240 may be hermetically sealed. For example, the inner diameter of barrier plate 240 may be sealed to sleeve 310, whereas the outer diameter of barrier plate 240 is sealed to weld ring 300. Barrier plate 240 may include a relatively thin material to provide the best magnetic performance for pump 100 while maintaining sufficient strength and stiffness to isolate electromagnetic coil 250 and magnetic cup 260 from the flow path.

Piston/pole assembly 220 includes piston 320 and pole 330. Piston/pole assembly 220 is positioned such that piston 320 is located within central aperture 280 of magnetic cup 260. Piston spring 230 is located within central aperture 280 adjacent one end of piston 320. Piston spring 230 functions to bias piston/pole assembly 220 away from electromagnetic coil 250 and magnetic cup 260 such that pole 330 is spaced apart from barrier plate 240. Piston 320 may be interference fit to pole 330 or secured to pole 330 by other suitable techniques. Pole 330 comprises a magnetic material that is attracted to magnetic cup 260 to produce a pump stroke. Because pole 330 is within the fluid flow path, the material of pole 330 may be configured to resist corrosion. As an example, pole 330 may include a magnetic stainless steel alloy, such as AL29-4. Likewise, piston 320 is also located within the fluid flow path and may therefore also be configured to resist corrosion. As an example, piston 320 may include a sapphire material, which can limit wear between piston and sleeve 310 caused by the pumping action of fluid delivery pump 100. As other examples, piston 320 may include a metal material, such as a stainless steel or titanium alloy. In some examples, piston/pole assembly 220 may include a unitary component consisting of a single magnetic material such as a stainless steel alloy.

Cover 120 mounts to barrier plate 240 to form an enclosure containing piston/pole assembly 220 and spring 230. When fluid delivery pump 100 is fully-assembled, cover 120 is secured to bulkhead 110 within mounting bay 112. As examples, cover 120 may be interference fit within mounting bay 112 or secured to bulkhead 110 using a weld joint, one or more screws or other techniques.

Piston/pole assembly 220 actuates within an enclosure between base 190 of cover 120 and barrier plate 240. Piston spring 230 biases piston/pole assembly 220 away from check valve 140 and against base 190 of cover 120. The motion of piston/pole assembly 220 is driven by electromagnetic coil 250. Specifically, during a pump stroke, current through electromagnetic coil 250 serves to magnetize magnetic cup 260 to attract pole 330 of piston/pole assembly 220. The magnetic attraction force between pole 330 and magnetic cup 260 overcomes the force of piston spring 230 to create a pumping action of piston 320. The motion of piston 320 forces therapeutic agent within central aperture 280 of magnetic cup 260 through check valve 140. Following a pump stroke, current through electromagnetic coil 250 stops, and piston spring 230 returns piston/pole assembly 220 to its original position against base 190 of cover 120.

Therapeutic agent pushed by piston 320 during a pump stroke exits fluid delivery pump 100 through check valve 140. Check valve 140 is generally a one-way valve that is configured to allow a therapeutic agent to flow from pumping mechanism 130 through an exit port of the valve and to substantially prevent flow back into the pumping mechanism through the exit port. Check valve 140 includes disc 340, valve spring 350, and bonnet 360. Valve spring 350 functions to bias disc 340 against a seat in magnetic cup 260, e.g. in sleeve 310 of magnetic cup 260 (see FIG. 6). Bonnet 360 functions to hold spring 350 in place. Referring to FIG. 6, bonnet 360 includes exit port 370 that provides a fluid passageway through bonnet 360. When check valve 140 is closed, disc 340 seals to the seat in, e.g. sleeve 310 of magnetic cup 260. The configuration of check valve 140 may be referred to as a lift check valve. In other examples, different valve configurations may be used including, but not limited to, ball check valves, diaphragm valves, gate valves and other valves. The design of fluid delivery pump 100 allows different valves to be selected depending on, e.g. a particular therapeutic agent to be pumped through fluid delivery pump 100 and the desired pumping characteristics of pump 100.

As illustrated in FIG. 5 and more clearly in the section view of FIG. 6, accumulator 150 is arranged at the outlet of pump 100, i.e. at exit port 370 of check valve 140. Accumulator 150 includes cover 400 and diaphragm 410. Accumulator 150 is connected to bulkhead 110. As shown in FIG. 6, cover 400 of accumulator 150 is connected to bulkhead 110. In one example, cover 400 may be welded to bulkhead 110. Diaphragm 410 of accumulator 150 is connected to cover 400. In one example, diaphragm 410 may be welded to cover 400 to define a sealed chamber between diaphragm 410 and cover 400 within which a compressible gas may be stored. In operation of pump 100, diaphragm 410 may deflect under pressure generated by the therapeutic agent in the flow path pump 100 by compressing the gas between diaphragm 410 and cover 400. In one example, Helium may be introduced between diaphragm 410 and cover 400. In another example, Argon may be introduced between diaphragm 410 and cover 400. In another example, a combination of multiple gases may be introduced between diaphragm 410 and cover 400.

As fluid delivery pump 100 draws fluid from a reservoir or other source of a therapeutic agent through holes 200, filter 170 and holes 210 in base 190 of cover 120 into an enclosure of pumping mechanism 130 and pumps the fluid out of exit port 370 of check valve 140, diaphragm 410 of accumulator 150 deflects under the pressure generated by the therapeutic agent flowing through the flow path of the device in which accumulator 150 is employed. In this manner, accumulator 150 functions to provide compliance in the flow path of an IID to improve the accuracy of the metered delivery of therapeutic agent to a patient by pump 100 and reduce the energy required to drive the pump.

The combination of rigid cover 400 and flexible diaphragm 410 has several important advantages both in terms of manufacturability and performance of accumulator 150 within an IID, e.g. IID 12 of FIGS. 1 and 3A and 3B. Cover 400 acts to protect diaphragm 410 from plastic deformation and to also protect electronics and other components of the IID in which accumulator 150 is employed from coming into contact with the therapeutic agent flowing through the flow path of the device. Cover 400 is configured to withstand the pressure generated by the therapeutic agent in the flow path without deforming. For example, cover 400 is sized, shaped, and constructed from a material that allows the cover to withstand the pressure generated by the therapeutic agent in the flow path without appreciably deforming. During operation of pump 100 circumstances can arise, which may cause pump 100 to produce an over pressurization event in the flow path of the device. Under such over pressurization conditions, the pressure generated by the therapeutic agent in the flow path may exceed the design specifications for pump 100 as well as the IID in which the pump is employed.

During an over pressurization event, an accumulator including one or more thin diaphragms, e.g. like diaphragm 410, arranged at exit port 370 of valve 140 may be subjected to pressures that would cause the diaphragms to plastically, i.e., irreversibly, deform. Such plastic deformation of the diaphragm may change the operating characteristics of the device, including changing the amount of compliance the diaphragm provides to the flow path downstream of pump 100. Accumulator 150 according to this disclosure, however, includes cover 400 to guard against irreversible deformation of diaphragm 410 during operation of pump 100. Cover 400 is configured to act as a backstop to diaphragm 410 such that the diaphragm may not plastically deform during an over pressurization event of pump 100. Before reaching a threshold deflection at which plastic deformation will occur the diaphragm strikes cover 400, which, as noted above, is configured to withstand the pressure generated by the therapeutic agent in the flow path without appreciably deforming. In some examples, diaphragm 410 may experience some minor irreversible deformation during a high pressure event within pump 100. However, in such an example, cover 400 may nevertheless act to limit the deflection of diaphragm 410 such that any irreversible deformation does not significantly impact the ongoing function of diaphragm 410 to provide the proper amount of compliance to the flow path of pump 100.

As noted above, cover 400 may be welded to bulkhead 110. In one example, the connection between cover 400 and bulkhead 110, e.g., a weld joint, may form a hermetic seal to inhibit flow of the therapeutic agent from the flow path out through accumulator 150. The arrangement of pump 100 and bulkhead 110 may be employed in an IID in which electronics and other components sensitive to fluid contamination are located in the bulkhead outside of the flow path of the device. In such an example, the connection between cover 400 and bulkhead 110 may be configured to inhibit flow of the therapeutic agent from the flow path out through accumulator 150 and into contact with such electronics of the device in which pump 100 and bulkhead 110 are employed. Additionally, under some circumstances, an over pressurization event generated by pump 100 may generate sufficient pressures in the flow path of the device that without cover 400 acting as a backstop to diaphragm 410 the diaphragm may rupture and allow fluid to flow out through accumulator 150 into contact with, e.g. electronics of the IID in which the accumulator is employed. Thus, cover 400 may act to protect components of the IID in which accumulator 150 is employed from contamination by the therapeutic agent flowing through the flow path of the device.

Cover 400 may also improve the manufacturability of accumulator 150. An accumulator employed in an IID may include, instead of cover 400 and diaphragm 410, two thin, flexible diaphragms connected to one another to define a gas chamber there between. Such a design, however, may necessitate edge welding the two thin diaphragms to one another, which may be complex and costly. The combination of cover 400 and diaphragm 410 of accumulator 150 in accordance with examples of this disclosure allows attaching the thin, flexible diaphragm 410 to the relatively thick cover 400, which acts as a rigid substrate that is less complex and less expensive to which to weld diaphragm 410.

Figure 7A:
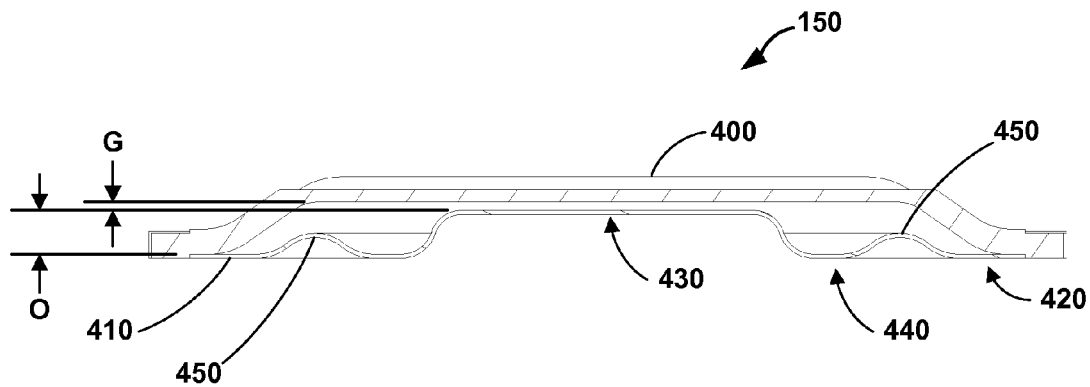
FIG. 7A is a section view of an example accumulator in accordance with this disclosure.
Figure 7B:
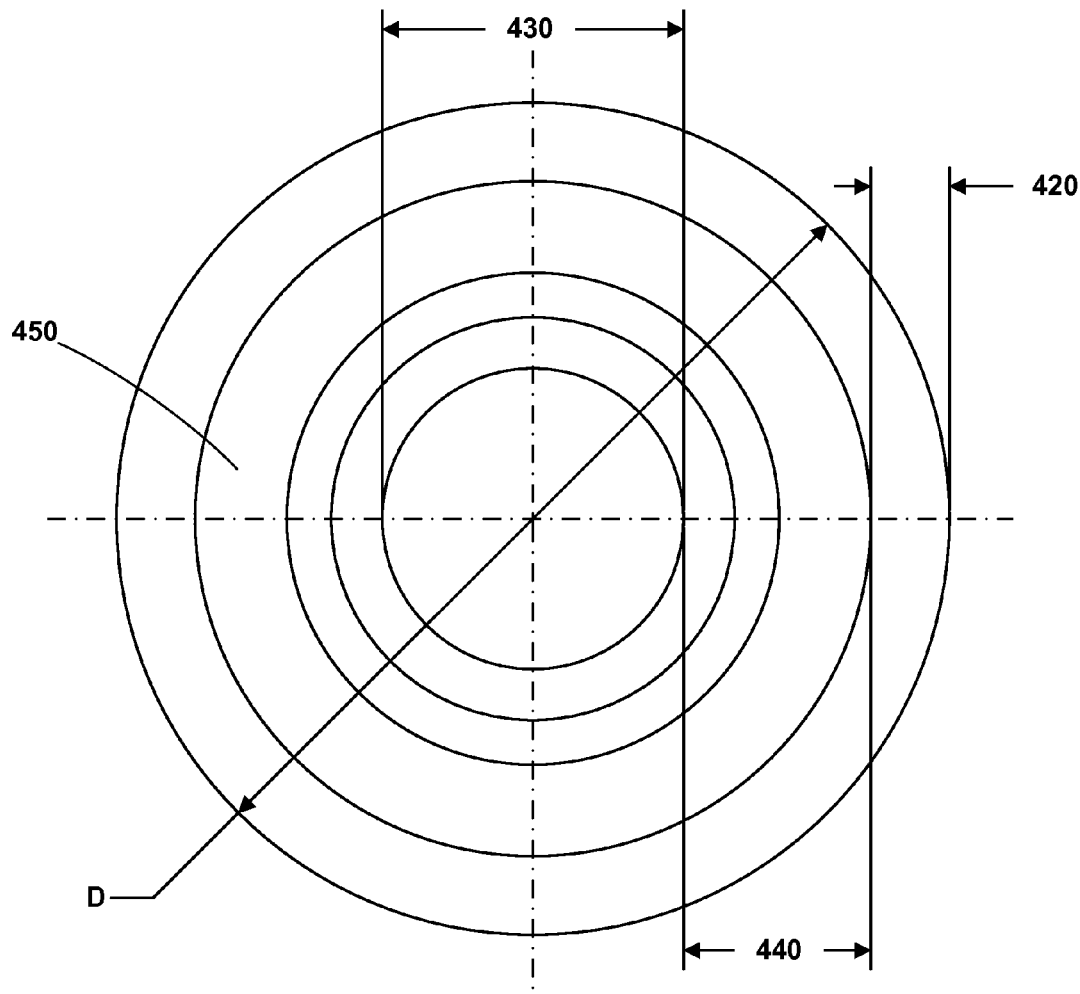
FIG. 7B is a plan view of the diaphragm of the accumulator of FIG. 7A.

FIGS. 7A and 7B illustrate accumulator 150 in greater detail, including the section view of cover 400 connected to diaphragm 410 in FIG. 7A and the plan view of diaphragm 410 in FIG. 7B. As illustrated in FIGS. 7A and 7B, diaphragm 410 is a corrugated diaphragm. As further illustrated in FIG. 7B, diaphragm 410 is a disc shaped corrugated diaphragm. In other examples, a diaphragm employed in an accumulator according to this disclosure may have a variety of shapes and configurations, including an oval or rectilinear shaped diaphragm with none or one or more corrugations. Diaphragm 410 includes a number of regions including rim 420, hub 430, and web 440. Rim 420 defines the periphery of disc shaped corrugated diaphragm 410. Hub 430 defines a central portion of diaphragm 410 that is generally parallel to and offset from rim 420. As illustrated in FIG. 7A, hub 430 is parallel to and offset from rim 420 by an offset distance, O. Web 440 is the remaining portion of diaphragm 410 connecting rim 420 to hub 430. Web 440 includes corrugation 450. Corrugation 450 is a ring-shaped protrusion (or depression depending on which side of diaphragm 410 corrugation 450 is viewed from) protruding from web 440 of diaphragm 410.

In addition to the advantages afforded by the combination rigid cover and flexible diaphragm of accumulators in accordance with this disclosure, the arrangement of the accumulator within an IID may change the effect the accumulator has on the performance of the pump of the IID. In some examples, arranging the accumulator close to the outlet of the pump of an IID may have a greater beneficial effect on the performance of the pump than arranging the accumulator further downstream of the outlet of the pump. As noted above, accumulator 150 is arranged at exit port 370 of check valve 140 of pump 100. FIG. 5 illustrates that, in the example of accumulator 150 and pump 100, hub 440 of disc shaped diaphragm 410 is centrally aligned with exit port 370 of check valve 140 and is arranged immediately adjacent exit port 370, e.g. without any intervening structures between hub 440 and port 370. The offset distance, O, between rim 420 and hub 440 of diaphragm 410 may be selected at least in part to accommodate check valve 140 such that exit port 370 is nested in hub 440 of diaphragm 410. Thus, the arrangement of exit port 370 of check valve 140 with respect to diaphragm 410 may be selected to substantially immediately translate pressure generated by the therapeutic agent flowing from pumping mechanism 130 of pump 100 through the exit port is to diaphragm 410 of accumulator 150. Arranging accumulator 150 with respect to the outlet of pump 100, i.e. with respect to exit port 370 of valve 140 may increase the beneficial effect the compliance generated by deflection of diaphragm 410 has on the performance of pump 100, including increasing the accuracy and repeatability of the metered flow of therapeutic agent supplied by the pump and decreasing the power requirements for operating the pump.

As noted above, cover 400 of accumulator 150 is configured to act as a backstop to diaphragm 410 such that the diaphragm may not plastically deform during an over pressurization event of pump 100 because before reaching a threshold deflection at which plastic deformation will occur diaphragm 410 strikes cover 400, which, as noted above, is configured to withstand the pressure generated by the therapeutic agent in the flow path without appreciably deforming. Thus, the gap distance, G, defining the offset between hub 440 of diaphragm 410 and cover 400 may be selected such that cover 400 stops diaphragm 410 before the diaphragm is plastically deformed under the pressure generated by the therapeutic agent in the flow path. In other words, if the gap distance, G, is too large, there may be a risk that diaphragm 410, under pressure generated by an agent in the flow path, continues to deflect past the point of reaching plastic deformation before striking cover 400. Additionally, the gap distance, G, defining the offset between hub 440 of diaphragm 410 and cover 400 may be selected such that diaphragm 410 does not strike cover 400 without deflecting enough to provide the proper compliance to the flow path of the device in which accumulator 150 is employed. In other words, if the gap distance, G, is too small, there may be a risk that diaphragm 410 under pressure generated by an agent in the flow path fails to deflect enough to provide enough compliance to the flow path. Thus, based on the particular diaphragm, e.g., shape, configuration in terms of corrugations and other features like a flat central hub, material, etc., of an example accumulator in accordance with this disclosure, a particular gap distance, G, between the diaphragm and the cover of the accumulator may be selected to substantially prevent plastic deformation of the diaphragm. Additionally, the diaphragm configuration and gap distance, G, between the diaphragm and the cover of an accumulator according to this disclosure may be selected to allow the diaphragm to deflect enough without contacting the cover such that deflection of the diaphragm provides the proper compliance to the flow path in which the accumulator is arranged.

Accumulators according to this disclosure are configured to provide compliance to the flow path of an IID within which the accumulator is employed. The amount of compliance that is appropriate for and beneficial for a particular IID may depend on the operating parameters of the pump of the IID. For example, an optimal or optimized compliance for a particular IID may be characterized by a compliance value or range of values that are based at least in part on a stroke volume of the fluid delivery pump of the IID.

The compliance of a particular accumulator, e.g. accumulator 150 will be a function of the amount of fluid volume the accumulator will absorb at a particular pressure, which is a function of the amount the diaphragm of the accumulator will deflect at the applied pressure. Thus, the compliance of an accumulator according to this disclosure, e.g. accumulator 150 may be a function of the shape, sizing, and material of the diaphragm of the accumulator, e.g. diaphragm 410. Referring to example accumulator 150, the compliance provided to the flow path of the IID within which accumulator 150, e.g. IID 12, may be a function of the shape, sizing, and material of diaphragm 410. In one example, the material selected for diaphragm 410 may be selected based at least in part on the mechanical properties of the material, e.g. based on stress and strain limits such as the modulus of elasticity, or Young's modulus of the material. In addition to material, the geometrical shape of diaphragm 410 may affect the compliance provided by accumulator 150 at a particular operating pressure of pump 100. For example, the diameter, D, of disc shaped diaphragm 410 as illustrated in FIG. 7B may be selected to vary the amount of compliance provided by accumulator 150. In one example, the thickness of diaphragm 410 may be selected to vary the amount of compliance provided by accumulator 150. In one example, the position of and number of corrugations in web 440 of diaphragm 410 may also be selected to vary the amount of compliance provided by accumulator 150. Additionally, the overall geometric configuration of diaphragm 410 or another diaphragm in accordance with this disclosure may be configured to vary the amount of compliance provided by accumulator 150. For example, the configuration of a peripheral rim portion, central hub portion, and connecting web portion of a diaphragm, as well as the arrangement of the hub offset from the rim may be changed to modulate the proper amount of compliance for a particular pump of an IID within which an accumulator according to this disclosure is employed.

As described above, the specific geometric and material properties of cover 400 and diaphragm 410 may be driven by a number of characteristics of a particular configuration of IID within which they are employed, including, e.g. stroke volume, the operating pressure of pump 100, a target compliance within the flow path of the device, and a number of other parameters. Thus the particular shape, size, and material of cover 400 and diaphragm 410 may vary in different examples according to this disclosure depending on the characteristics of the pump and IID with which they are employed. In one example, if the volumetric output of pump 100 per stroke increases, it may be necessary to change the gap distance, G, between diaphragm 410 and cover 400, as well as diaphragm thickness, diameter, D, material, and number of convolutions 450 in order to provide the proper amount of compliance to the flow path of the device. Employing an accumulator according to this disclosure with the proper amount of compliance for a particular IID may involve determining a peak pressure anticipated during dynamic strokes of a particular volumetric output and designing a diaphragm to provide the proper compliance to the flow path and including a cover configured and arranged with respect to the diaphragm to reduce the risk the diaphragm is irreversibly deformed during an overpressurization event. As noted above, diaphragm diameter, thickness, the number of convolutions, and gap between the diaphragm and cover may all be varied to modulate the performance of an accumulator for a particular IID.

In one example, an accumulator according to this disclosure may be configured to withstand pressures up to approximately 100 pounds per square inch (psi) without a substantial change in fatigue life or static compliance of the accumulator. In such an example, cover 400 and diaphragm 410 may be both fabricated from Titanium or a Titanium alloy, and cover 400 may be approximately 0.305 millimeters (0.012 inches) thick and diaphragm 410 approximately 0.051 millimeters (0.002 inches) thick. Additionally, in this example, the gap distance, G, defining the offset between hub 440 of diaphragm 410 and cover 400 may be approximately equal to 0.102 millimeters+/−0.051 millimeters (0.004 inches+/−0.002 inches) with the diameter, D, of diaphragm 410 approximately equal to 10.2 millimeters (0.400 inches). The stiffness and therefore compliance of diaphragm 410 may generally depend on the thickness and diameter, D, of the diaphragm. Thus, if the diameter, D, of diaphragm 410 is made smaller, it may be necessary to also reduce the thickness and/or increase the gap distance, G, between diaphragm 410 and cover 400. Conversely, if the diameter, D, of diaphragm 410 is made larger, it may be necessary to increase the thickness of the diaphragm. However, the gap distance, G, between diaphragm 410 and cover 400 may be limited by manufacturing tolerances such that it can only be reduced to a threshold offset between diaphragm and cover, in which case the adjustment in diameter, D, of diaphragm 410 may need to be accommodated to a greater extend by an increase in thickness than by a reduction in the gap distance, G.

FIGS. 8A-8D are section views of a number of alternative accumulators according to this disclosure, including different configurations such as some of the variations described above. In the example of 8A, accumulator 500 includes cover 510 and diaphragm 520. Diaphragm 520 of accumulator 500 is similar to diaphragm 410 including peripheral rim 530, central hub 540, and web 550 connecting the rim and hum. Web 550 of diaphragm 520, however, includes two corrugations 560 instead of the one corrugation 450 of diaphragm 410.

Figure 8A:
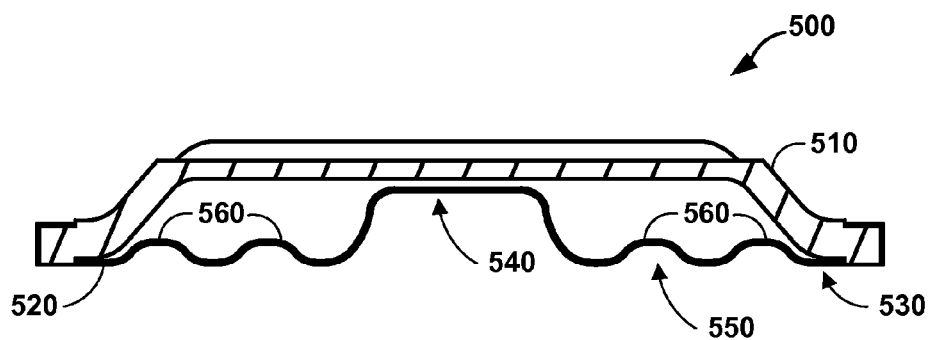
FIGS. 8A-8D are section views of a number of example accumulators in accordance with this disclosure.
Figure 8B:
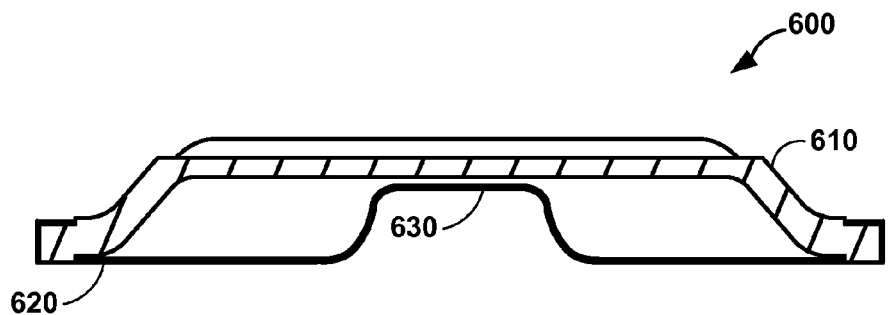

In the example of FIG. 8B, accumulator 600 includes cover 620 and diaphragm 620. Diaphragm 620, instead of including one or more corrugations between the periphery and central portion of the diaphragm, includes a single depression 630 in the central region of the diaphragm similar to hub 430 of diaphragm 410 and hub 540 of diaphragm 520.

Figure 8C:
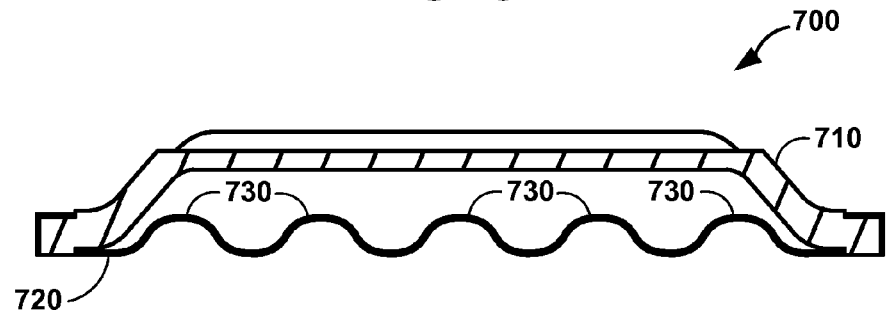

In the example of FIG. 8C, accumulator 700 includes cover 710 and diaphragm 720. Diaphragm 720 includes a plurality of corrugations 730 distributed across the surface of the diaphragm. In the examples of diaphragm 410 and 520, corrugation 450 and corrugations 560 are generally ring-shaped corrugations generally concentric with the disc-shaped diaphragms (see FIG. 7B illustrating ring-shaped protrusion 450). Diaphragm 720 illustrates a different configuration in that corrugations 730 are linear corrugations extending between opposite edges of disc-shaped diaphragm 720. In another example, a diaphragm similar to diaphragm 720 may instead include a plurality of ring-shaped, concentric corrugations that are positioned at different radial positions with respect to the center of the diaphragm. In the foregoing examples all of the illustrated corrugations have an arcuate shape, e.g., the arcuate shape of corrugations 450, 560, and 730 of FIGS. 7A, 8A, and 8C, respectively. However, in other examples according to this disclosure a corrugated diaphragm employed in an accumulator may include differently shaped corrugations, including, e.g., corrugations with a rectilinear profile shape.

Figure 8D:
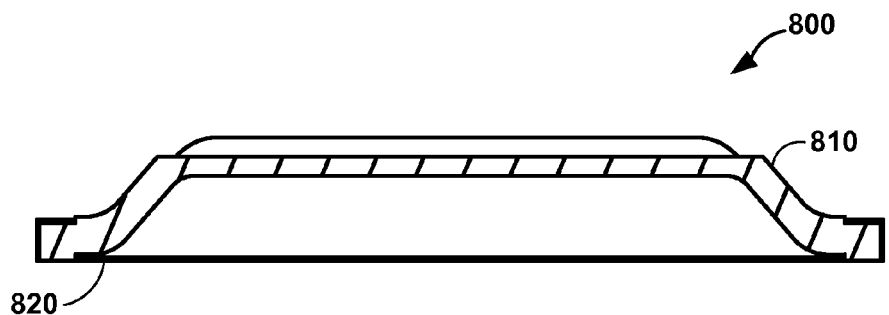

In FIG. 8D, accumulator 800 includes cover 810 and diaphragm 820. Diaphragm 820 of example accumulator 800 is a generally flat, planar disc-shaped diaphragm without any corrugations.

The example accumulators and associated diaphragms of FIGS. 8A-8D illustrate different characteristics that may be varied to modulate the compliance provided by accumulators according to this disclosure, but other variations are also possible. For example, the diameter or other dimensional parameters, e.g., thickness, of the accumulators may be varied to modulate compliance. In some cases, the diameter of a disc-shaped diaphragm may be the most influential parameter on the compliance provided by an accumulator including the diaphragm. However, if the diameter of the diaphragm is set as a function of the device, e.g. based on size constraints or the configuration of the pump the outlet of which defines the location of the accumulator, then material properties, including Young's modulus and thickness may appreciably affect the compliance provided by the accumulator including the diaphragm.

If the diaphragm includes corrugations, then the number of corrugations and position, e.g. radial position or radius/diameter of ring shaped corrugation may most affect the compliance provided. Different materials may be employed to change the mechanical properties of the diaphragm, e.g. stress/strain limits like Young's modulus. In one example, diaphragms and/or covers included in accumulators according to this disclosure may be fabricated from a number of different biocompatible materials including, e.g., stainless steel, titanium, or a biocompatible polymer. In one example, the cover and diaphragm of an accumulator according to this disclosure are fabricated from the same material and in another example the cover and diaphragm are fabricated from different materials. In one example, the cover and/or diaphragm of an accumulator according to this disclosure are fabricated from an American Society for Testing and Materials (ASTM) grade 2 titanium standards for which are set by ASTM International of West Conshohocken, Pa.

As the compliance of an accumulator according to this disclosure, may be a function of the shape, sizing, and material of the diaphragm of the accumulator and the compliance for a particular IID may be selected based on operating parameters of the pump of the IID, so may the shape, sizing, and material of the diaphragm of an accumulator according to this disclosure may be selected based on an operational parameter of the pump, including based on the stroke volume of the pump as described above. In one example, the configuration of the diaphragm of an accumulator according to this disclosure, e.g. the size, shape, and material of the diaphragm is varied to provide compliance in a flow path of an IID that is greater than or equal to a stroke volume of the pumping mechanism of the pump of the IID. In such cases under normal operating conditions of the IID, the accumulator will be configured to absorb at least the entire volume of one stroke of the pump. While configuring an accumulator to provide compliance that is greater than the stroke volume of the pump of the IID may be beneficial under certain limited operational circumstances, there may be a threshold compliance level beyond which any benefit becomes negligible or even the compliance becomes inappropriately large for the particular IID. As such, in one example, the configuration of the diaphragm of an accumulator according to this disclosure is varied to provide compliance in a flow path of an IID that is not greater than 10 times a stroke volume of the pumping mechanism of the pump of the IID within which the accumulator is employed.

As noted above, accumulators according to this disclosure may provide a number of advantages that improve the operation of IIDs within which such accumulators are employed. For example, accumulators in accordance with this disclosure may increase the accuracy of pulses of therapeutic agent delivered by the pump of an IID and the repeatability by which the pump delivers the agent to a patient. Additionally, the energy required to pump the therapeutic agent from the IID to the patient may be reduced by employing accumulators in accordance with foregoing examples.

Several tests were conducted of accumulators in accordance with this disclosure to measure the affect the accumulator had on pump performance. The tests included a number of test IIDs including pumps generally intended to operate in a manner similar to the examples described above. The test IIDs as fabricated included rigid, non-compliant covers over the check valve exit port defining the outlets of the pumps of the IIDs. Each of a number of as built IIDs was tested by pumping water through the flow path of the IID and out a pipette connected to the device. The amount of fluid delivered out of the pipette per stroke of the pump was measured, as well as the energy required to operate the pump.

After testing the as built IIDs, the rigid, non-compliant valve cover of each device was machined away to defining an opening over which a flexible diaphragm may be placed to act as an accumulator in the flow path of the IID. The rigid accumulator cover described above in association accumulators according to this disclosure was not employed in the test units because over pressurization and fluid contamination were not concerns of or the subject of the tests. A test diaphragm design was bonded, with an epoxy, into the opening directly above the pump outlet, i.e., the exit port of the check valve of the pump. The test diaphragm employed was a disc-shaped diaphragm including three concentric ring-shaped corrugations generally evenly distributed from toward a periphery to toward a center of the diaphragm. The test diaphragms were fabricated from ASTM grade 2 titanium and had a diameter approximately equal to 0.402 inches+/−0.004 inches. The thickness of the diaphragms varied from between approximately 0.0019 to 0.00255 inches. The corrugations in the diaphragms included a generally arcuate profile in accordance with corrugation 450 of example diaphragm 410 illustrated in FIGS. 6 and 7A and corrugations 730 in example diaphragm 720 of FIG. 8C. Each corrugation included a height approximately equal to 0.010+/−0.002 inches and a width approximately equal to 0.057+/−0.001 inches. The modified IIDs with flexible diaphragms at the outlets of the pumps were tested in a manner similar to the as built IIDs. Each of the modified IIDs was tested by pumping water through the flow path of the IID and out a pipette connected to the device. The amount of fluid delivered out of the pipette per stroke of the pump was measured, as well as the energy required to operate the pump.

The modified IIDs including the flexible diaphragm in the flow path of the device exhibited a number of significant performance gains over the as built IIDs. In a series of tests as set forth above, the modified IIDs exhibited an average 5.5% increase in stroke volume of fluid per stroke pumped, thus increasing the actual stroke volume of the pump of the IID closer to the designed nominal stroke volume, which in the case of the tested IIDs was 1 micro liter. For example, one as built IID tested delivered 0.693 micro liters of fluid per stroke, while the same IID modified to include a flexible diaphragm delivered 0.7402 micro liters of fluid per stroke, representing a 6.8% increase in stroke volume. At the same time, the modified IIDs exhibited an average 7.1% decrease in energy (millijoules) per micro liter of fluid delivered. The modified IIDs also exhibited an average 2.1% decrease in the energy (millijoules) required to pump one stroke of fluid. Additionally, the range of volumetric change between strokes, a measure of the repeatability of pump performance per stroke, was compared for the as built and modified IIDs. The modified IIDs exhibited an average 6% decrease in the range of volumetric change between pump strokes. Thus, the modified IIDs including a flexible diaphragm arranged and configured in accordance with this disclosure exhibited greater stroke volume accuracy and repeatability, while reducing the amount of energy required to pump each stroke of fluid through the flow path of the tested devices.

In addition to measuring improvements in stroke volume and energy consumption from a test IID without an accumulator according to this disclosure and a modified test IID with a flexible diaphragm in accordance with this disclosure, as built and modified IIDs were tested to measure peak pressure in the flow path of the device downstream of the pump. The accumulator employed in the modified IIDs for peak pressure tests included a diaphragm in accordance with example diaphragm 410 illustrated in FIG. 7A. Peak pressure in the flow path of the IIDs downstream of the pump was measured using a commercially available pressure transducer connected to a needle that was inserted into the catheter access ports of the devices. The pressure transducer employed in the tests was an EPX-NO miniature threaded stainless steel diaphragm pressure sensor sold by Measurement Specialists of Hampton, Va. (formerly Entran Devices, a New Jersey and Les Clayes-sous-Bois, France based company). Two IIDs were tested as built without an accumulator arranged at the outlet of the pump and four modified IIDs including a flexible diaphragm were tested. On average, the addition of the flexible diaphragm to provide compliance in the flow path of the device decreased the maximum pressure in the flow path normalized for stroke volume (e.g. flow path pressure per micro liter of fluid pumped) from 15.93 to 5.13 pounds per square inch per micro liter of fluid, which represented approximately a 68% average decrease in the peak pressure in the flow path of the modified IIDs including the flexible diaphragms. Thus, the addition of the flexible diaphragm at the outlet of the pump of the IID functioned to soften flow path downstream of the outlet, thereby allowing the pump to complete a stroke without developing larger downstream pressures.

Techniques described in this disclosure associated with control electronics of an IID or external device, such as an external programmer may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. An implantable infusion device (IID) comprising:
   a reservoir configured to store a therapeutic agent;
   a fluid delivery pump configured to receive the therapeutic agent from the reservoir and deliver the therapeutic agent through an outlet of the fluid delivery pump into a flow path; and
   an accumulator arranged at the outlet of the fluid delivery pump, the accumulator comprising:
   a cover; and
   a diaphragm biased away from the cover and configured to deflect toward the cover under pressure generated by the therapeutic agent in the flow path of the IID,
   wherein the cover is configured to withstand the pressure generated by the therapeutic agent in the flow path without appreciably deforming.

2. The IID of claim 1, wherein at least one of the cover and the diaphragm comprises at least one of stainless steel, titanium, or a biocompatible polymer.

3. The IID of claim 1, wherein the diaphragm comprises a corrugated diaphragm.

4. The IID of claim 1, wherein the diaphragm comprises a first thickness approximately equal to 0.051 millimeters (0.002 inches) and the cover comprises a second thickness approximately equal to 0.305 millimeters (0.012 inches).

5. The IID of claim 1, wherein the diaphragm comprises a disc shape.

6. The IID of claim 5, wherein the disc shaped diaphragm comprises:
a rim defining a periphery of the disc shaped diaphragm;
a hub defining a central portion of the disc shaped diaphragm that is generally parallel to and offset from the rim; and
a web connecting the rim and the hub.

7. The IID of claim 6, wherein the web comprises at least one corrugation.

8. The IID of claim 6, wherein the outlet comprises:
a check valve configured to allow flow from the pumping mechanism into the catheter through an exit port and to substantially prevent flow from the catheter into the pumping mechanism through the exit port,
wherein the hub is offset from the rim to accommodate the check valve such that the exit port of the check valve is nested in the hub of the disc shaped diaphragm.

9. The IID of claim 1, wherein the diaphragm is arranged with respect to the outlet such that the diaphragm is immediately adjacent the outlet with no intervening structures between the diaphragm and the outlet.

10. The IID of claim 9, wherein the diaphragm is arranged with respect to the outlet such that pressure generated by the therapeutic agent flowing from the pumping mechanism through the outlet is substantially immediately translated to the diaphragm.

11. The IID of claim 1, wherein the diaphragm is offset from the cover by a first distance, and wherein the first distance is selected such that the cover stops the diaphragm before the diaphragm is plastically deformed under the pressure generated by the therapeutic agent in the flow path of the IID.

12. The IID of claim 1, wherein at least one of a shape, material, and size of the diaphragm is selected based on an operational parameter of the fluid delivery pump.

13. The IID of claim 1, wherein the fluid delivery pump comprises a piston pumping mechanism.

14. The IID of claim 13, wherein at least one of a shape, material, and size of the diaphragm is selected based on a stroke volume of the piston pumping mechanism.

15. The IID of claim 14, wherein at least one of a shape, material, and size of the diaphragm is selected such that the accumulator is configured to provide compliance to the flow path that is greater than or equal to 1 times but not more than 10 times the stroke volume of the piston pumping mechanism.

16. A fluid delivery pump for an implantable infusion device (IID), the fluid delivery pump comprising:
an inlet configured to be fluidically connected to a source of a therapeutic agent;
an outlet configured to be fluidically connected to a catheter;
a pumping mechanism configured to receive the therapeutic agent from the source through the inlet and deliver the therapeutic agent through a flow path from the outlet into and through the catheter; and
an accumulator arranged at the outlet, the accumulator comprising:
a cover; and
a diaphragm biased away from the cover and configured to deflect toward the cover under pressure generated by the therapeutic agent in the flow path of the IID,
wherein the cover is configured to withstand the pressure generated by the therapeutic agent in the flow path without appreciably deforming.

17. The fluid delivery pump of claim 16, wherein at least one of the cover and the diaphragm comprises at least one of stainless steel, titanium, or a biocompatible polymer.

18. The fluid delivery pump of claim 16, wherein the diaphragm comprises a corrugated diaphragm.

19. The fluid delivery pump of claim 16, wherein the diaphragm comprises a first thickness approximately equal to 0.051 millimeters (0.002 inches) and the cover comprises a second thickness approximately equal to 0.305 millimeters (0.012 inches).

20. The fluid delivery pump of claim 16, wherein the diaphragm comprises a disc shape.

21. The fluid delivery pump of claim 20, wherein the disc shaped diaphragm comprises:
a rim defining a periphery of the disc shaped diaphragm;
a hub defining a central portion of the disc shaped diaphragm that is generally parallel to and offset from the rim; and
a web connecting the rim and the hub.

22. The fluid delivery pump of claim 21, wherein the web comprises at least one corrugation.

23. The fluid delivery pump of claim 21, wherein the outlet comprises:
a check valve configured to allow flow from the pumping mechanism into the catheter through an exit port and to substantially prevent flow from the catheter into the pumping mechanism through the exit port,
wherein the hub is offset from the rim to accommodate the check valve such that the exit port of the check valve is nested in the hub of the disc shaped diaphragm.

24. The fluid delivery pump of claim 16, wherein the diaphragm is arranged with respect to the outlet such that the diaphragm is immediately adjacent the outlet with no intervening structures between the diaphragm and the outlet.

25. The fluid delivery pump of claim 24, wherein the diaphragm is arranged with respect to the outlet such that pressure generated by the therapeutic agent flowing from the pumping mechanism through the outlet is substantially immediately translated to the diaphragm.

26. The fluid delivery pump of claim 16, wherein the diaphragm is offset from the cover by a first distance, and wherein the first distance is selected such that the cover stops the diaphragm before the diaphragm is plastically deformed under the pressure generated by the therapeutic agent in the flow path of the IID.

27. The fluid delivery pump of claim 16, wherein at least one of a shape, material, and size of the diaphragm is selected based on an operational parameter of the fluid delivery pump.

28. The fluid delivery pump of claim 16, wherein the pumping mechanism comprises a piston pumping mechanism.

29. The fluid delivery pump of claim 28, wherein at least one of a shape, material, and size of the diaphragm is selected based on a stroke volume of the piston pumping mechanism.

30. The fluid delivery pump of claim 29, wherein at least one of a shape, material, and size of the diaphragm is selected such that the accumulator is configured to provide compliance to the flow path that is greater than or equal to 1 times but not more than 10 times the stroke volume of the piston pumping mechanism.

31. A system comprising:
an implantable infusion device (IID); and
a catheter connected to the IID,
wherein the IID comprises:
a reservoir configured to store a therapeutic agent;
a fluid delivery pump configured to receive the therapeutic agent from the reservoir and deliver the therapeutic agent through a flow path from an outlet of the fluid delivery pump into and through the catheter; and an accumulator arranged at the outlet of the fluid delivery pump, the accumulator comprising:

a cover; and a diaphragm biased away from the cover and configured to deflect toward the cover under pressure generated by the therapeutic agent in the flow path of the IID, wherein the cover is configured to withstand the pressure generated by the therapeutic agent in the flow path without appreciably deforming.

* * * * *